United States Patent [19]

Immel et al.

[11] Patent Number: 5,196,592
[45] Date of Patent: Mar. 23, 1993

[54] PROCESS FOR THE PREPARATION OF DIPHENYLAMINES

[75] Inventors: Otto Immel, Krefeld; Helmut Waldmann, Leverkusen; Reinhard Langer, Krefeld; Gerhard Darsow, Krefeld; Hans-Josef Buysch, Krefeld, all of Fed. Rep. of Germany

[73] Assignee: Bayer Aktiengesellschaft, Leverkusen, Fed. Rep. of Germany

[21] Appl. No.: 805,441

[22] Filed: Dec. 11, 1991

[30] Foreign Application Priority Data

Jan. 10, 1991 [DE] Fed. Rep. of Germany ....... 4100514
Jan. 16, 1991 [DE] Fed. Rep. of Germany ....... 4101066

[51] Int. Cl.$^5$ ........................................... C07C 209/52
[52] U.S. Cl. ..................................... 564/415; 564/433
[58] Field of Search ................................ 564/415, 433

[56] References Cited

FOREIGN PATENT DOCUMENTS 0208933 1/1987 European Pat. Off. .
0325132 7/1989 European Pat. Off. .
2331878 1/1974 Fed. Rep. of Germany .
2520893 11/1976 Fed. Rep. of Germany .

*Primary Examiner*—Raymond Richard L.
*Attorney, Agent, or Firm*—Sprung Horn Kramer & Woods

[57] ABSTRACT

Diphenylamine, which can be substituted by lower alkyl and/or lower alkoxy, is obtained from the corresponding N-cyclohexylidene-aniline by catalytic dehydrogenation, a rhodium-containing catalyst being employed.

20 Claims, No Drawings

PROCESS FOR THE PREPARATION OF DIPHENYLAMINES

BACKGROUND OF THE INVENTION

1. Field of the Invention

The invention relates to a process for the prepartion of diphenylamine, which can be substituted by lower alkyl and/or lower alkoxy, by dehydrogenation of the corresponding N-cyclohexylidene-aniline in the presence of a rhodium-containing supported catalyst.

2. Description of the Related Art

A process in which imines, such as N-cyclohexylideneaniline and derivatives thereof, are used as starting substances and are dehydrogenated in the gas phase in the presence of supported catalysts based on nickel, platinum, palladium or copper-chromium is known for the preparation of diphenylamine and derivatives thereof from German Offenlegungsschrift 2,331,878. The disadvantages of this process are the inadequate selectivity of the catalysts and their low stability under load, so that the yield of diphenylamine decreases greatly after only a few hours.

Nickel-chromium mixed catalysts which contain aluminium, copper and alkaline earth metal sulphates and alkali metal sulphates as secondary constituents, and nickelchromium mixed catalysts with addition of manganese and aluminium are described in German Offenlegungsschrift 2,520,893. The catalysts described achieve very high service lives of up to 6000 hours only under a hydrogen atmosphere, but the conversion and the selectivity are unsatisfactory. The service lives are considerably shorter in a carrier stream of inert gas, and, depending on the temperature, either significant amounts of cyclohexylaniline or carbazole occur as a troublesome by-product, in addition to methyldiphenylamine, which is difficult to remove. Further disadvantages of the catalysts described are their low stability under load and their limited ease of regeneration, which restricts their value for industrial use.

EP 208,933 describes rhodium supported catalysts, the particular feature of which is pretreatment of the support material with chromium salts and manganese salts. These catalysts are described as being suitable contacts for gas phase hydrogenation of completely or partially hydrogenated, optionally substituted hydroxydiphenyls, the reaction being carried out in a hydrogen atmosphere, that is to say without a carrier stream of inert gas. The selectivities in the dehydrogenations of 2-cyclohexylidene/2-cyclohexenyl-cyclohexanone mixtures described in the examples do not, in general, exceed the 92% mark.

German Offenlegungsschrift 3,801,754 describes rhodium supported catalysts, the particular feature of which is, in addition to pretreatment of the support material with chromium salts and manganese salts, additional doping with at least one metal from the group comprising palladium, platinum and iridium. These catalysts are described as being suitable ones for gas phase dehydrogenation of optionally substituted dicyclohexylamines to give the corresponding diphenylamines, the presence of cyclohexylanilines and aniline and that of ammonia being described as not troublesome. Hydrogen, nitrogen and alkanes can be employed as carrier gases.

In German Offenlegungsschrift 3,801,754, the processes described hitherto for diphenylamine synthesis starting from partially hydrogenated, optionally substituted diphenylamines, that is to say also the dehydrogenation of cyclohexylidene-anilines, are described as being inadequate for industrial use.

The inadequacies of the dehydrogenation of cyclohexylidene-anilines are to be seen in association with the limited chemical stability of this class of compounds, which tend to undergo self-condensation, aniline being split off and oligomeric cyclohexenyl compounds being formed. The limitation of German Offenlegungsschrift 3,801,754 to the very stable dicyclohexylamines is to be assessed against this background. Since exclusively catalysts based on the support material claimed in EP 208,933 are described in German Offenlegungsschrift 3,801,754, with the difference that in addition to rhodium, another platinum metal is precipitated onto the support material, it follows that the catalysts from EP 208,933 should be of only limited suitability, that is to say when certain substrates are used, for diphenylamine synthesis by dehydrogenation.

SUMMARY OF THE INVENTION

It has now been found, surprisingly, that both the catalysts described in EP 208,933 and those described in German Offenlegungsschrift 3,801,754 are particularly suitable for gas phase dehydrogenation of optionally symmetrically or non-symmetrically substituted N-cyclohexylideneanilines to give diphenylamines, troublesome side reactions largely being suppressed.

This is of particular industrial importance, because symmetrically and above all, non-symmetrically substituted N-cyclohexylidene-anilines are particularly easy to prepare from the corresponding components of cyclohexanone and aniline, water being split off.

It has now been found that diphenylamines of the formula

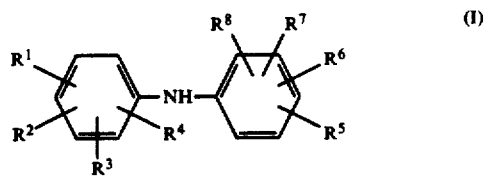

in which
- $R^1$ represents hydrogen, $C_1$–$C_6$-alkyl, $C_1$–$C_2$-alkoxy, $C_3$–$C_6$-cycloalkyl, benzyl or aryl,
- $R^2$ represents hydrogen, $C_1$–$C_6$-alkyl or $C_1$–$C_2$-alkoxy,
- $R^5$ denotes hydrogen, $C_1$–$C_6$-alkyl, $C_1$–$C_6$-alkoxy, $C_3$–$C_6$-cycloalkyl, benzyl, aryl, hydroxyl, amino, $C_1$–$C_6$-alkylamino, di-$C_1$–$C_6$-alkylamino, aryloxy or arylamino,
- $R^6$ represents hydrogen, $C_1$–$C_6$-alkyl, $C_1$–$C_6$-alkoxy, hydrogen, amino or $C_1$–$C_6$-alkylamino and
- $R^3$, $R^4$, $R^7$ and $R^8$ independently of one another denote hydrogen or $C_1$–$C_2$-alkyl, wherein aryl represents phenyl or represents 5- or 6-membered heteroaryl which has 1 or 2 hetero atoms from the group comprising N, O and S and is bonded in the 2-, 3- or 4-position, are obtained in a good yield and a high selectivity by a process in which cyclohexylidene-anilines of the formula

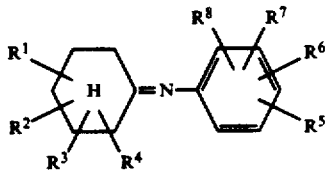

in which the radicals $R^1$ to $R^8$ have the above meaning, and which can be in admixture with a gaseous diluent are dehydrogenated at 250°-500° C. on a catalyst which has a rhodium content of 0.05–5% by weight, preferably 0.05–4% by weight, particularly preferably 0.1–3% by weight, it being possible for up to 90% by weight of the rhodium content to be replaced by one or more platinum metals from the group comprising palladium, platinum and iridium, and which furthermore contains additions of 1–6% by weight of an alkali metal hydroxide and 1–6% by weight of an alkali metal sulphate, all the percentages being based on the total weight of the catalyst.

DETAILED DESCRIPTION OF THE INVENTION

Alkyl radicals which may be mentioned are methyl, ethyl, propyl, isopropyl, butyl, isobutyl, tert.-butyl and hexyl, preferably methyl and ethyl.

Alkoxy radicals which may be mentioned are methoxy, ethoxy, propoxy, isoproxy, butoxy, isobutoxy, tert.-butoxy and hexyloxy, preferably methoxy and ethoxy. In the alkyl, alkoxy and alkyl(dialkyl)amino radicals the hydrocarbon parts may be straight-chain or branched.

Mononuclear isocyclic or heterocyclic aryl radicals which may be mentioned are furanyl, pyrrolyl, pyridyl and phenyl, preferably phenyl.

Condensation of anilines and cyclohexanones carrying identical or different substituents gives symmetrically or non-symmetrically substituted N-cyclohexylidene-anilines, for example N-cyclohexylidene-aniline, N-cyclohexylidene-2-methyl-aniline, N-cyclohexylidene-4-phenyl-aniline and N-2-methylcyclohexylidene-aniline; N-cyclohexylidene-aniline may be mentioned in particular.

Among the cyclohexylidene-anilines(II) those come into question for the inventive process which have a vapour pressure of at least 5 mbar, preferably at least 10 mbar, particularly preferably at least 20 mbar in the range of the reaction temperature, e.g. at 300° C.

Cyclohexylidene-anilines in which the aryl is phenyl are preferably employed. Cyclohexylidene-anilines which are furthermore preferably employed are those in which $R^4$ and $R^8$ denote hydrogen, particularly preferably those in which $R^3$, $R^4$, $R^7$ and $R^8$ denote hydrogen.

Preferred cyclohexylidene-anilines are furthermore those of the formula

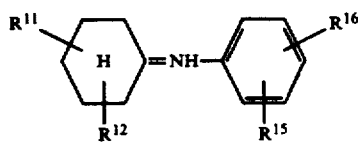

in which $R^{11}$ denotes hydrogen, $C_1$–$C_6$-alkyl, $C_1$–$C_2$-alkoxy, cyclopropyl, cyclopentyl, cyclohexyl or phenyl, $R^{12}$ denotes hydrogen, $C_1$–$C_2$-alkyl or $C_1$–$C_2$-alkoxy, $R^{15}$ denotes hydrogen, $C_1$–$C_6$-alkyl, $C_1$–$C_4$-alkoxy, cyclopropyl, cyclopentyl, cyclohexyl, phenyl, hydroxyl, amino, $C_1$–$C_6$-alkylamino, di-$C_1$–$C_4$-alkylamino, phenoxy or phenylamino and $R^{16}$ denotes hydrogen, $C_1$–$C_2$-alkyl or $C_1$–$C_2$-alkoxy.

Particularly preferred cyclohexylidene-anilines are those of the formula

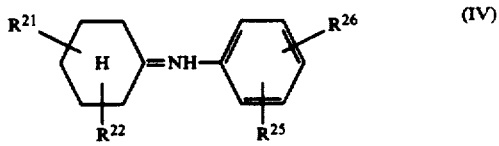

in which $R^{21}$, $R^{22}$ and $R^{26}$ independently of one another denote hydrogen, methyl or ethyl and $R^{25}$ represents hydrogen, methyl, ethyl, methoxy, ethoxy, $C_1$–$C_6$-alkylamino or di-$C_1$–$C_2$-alkylamino.

Possible carrier materials are the customary catalyst supports, such as α- and γ-aluminium oxides, aluminium spinels having the composition Me(II)Al$_2$O$_4$ or Me(I)AlO$_2$, wherein Me(II) is a divalent cation of iron, zinc, nickel, copper, cobalt, cadium, magnesium or others, preferably of magnesium, and Me(I) is a monovalent cation, for example of lithium (Li-Al spinel), kieselguhr, active charcoal, bentonite, silica gel, montmorillonites, ZrO$_2$, TiO$_2$, ZnO, MgO, rare earth oxides and pumices, preferably the aluminium oxides and aluminium spinels mentioned, particularly preferably γ-Al$_2$O$_3$. Such supports have a high specific surface area (>50 m$^2$, preferably >100 m$^2$/g). The supports particularly preferably have a content of chromium and manganese together of about 0.05–8% by weight, preferably 0.2–5% by weight, based on the total weight of the catalyst. The weight ratio of chromium to manganese is about 5:1–1:5, preferably 2:1–1:2. Such supports treated with chromium and manganese are known from German Offenlegungsschrift 3,801,754 and EP 208,933. The preparation and activation of these catalysts are therefore known to the expert.

The catalyst to be employed according to the invention contains rhodium or a combination of rhodium with another platinum metal from the group comprising palladium, platinum and iridium. The noble metals are present in a total amount of 0.05–5% by weight, preferably 0.05–4% by weight, particularly preferably 0.1–3% by weight, based on the total weight of the catalyst. In the case of a combination, up to 90% by weight of the rhodium can be replaced by one or more of the other platinum metals.

The catalyst to be employed furthermore contains 1–6% by weight, preferably 2–5% by weight, based on the total weight of the catalyst, of an alkali metal hydroxide, such as lithium hydroxide, sodium hydroxide, potassium hydroxide, rubidium hydroxide or caesium hydroxide, preferably lithium hydroxide, sodium hydroxide or potassium hydroxide, particularly preferably sodium hydroxide or potassium hydroxide. The catalyst to be employed furthermore additionally contains, in combination with one or more of the alkali metal hydroxides mentioned, 1–6% by weight, preferably 2–5% by weight, based on the total weight of the catalyst, of an alkali metal sulphate, such as lithium sulphate, sodium sulphate, potassium sulphate, rubidium sulphate or caesium sulphate, preferably lithium sulphate, sodium sulphate or potassium sulphate, particularly preferably sodium sulphate or potassium sulphate.

To prepare the catalysts described, in a particularly preferred procedure compounds of chromium and manganese are applied to an $Al_2O_3$ or an aluminium spinel in the form of extruded particles, pellets or beads having dimensions of about 2–10 mm, the support charged in this way is heated to an elevated temperature and the noble metals and one or more alkali metal hydroxides and one or more alkali metal sulphates are then applied separately; drying is carried out after every application, in general at 100°–140° C. under reduced to normal pressure, such as 1–1000 mbar, preferably 10–500 mbar, for example under a water pump vacuum.

In a particularly preferred manner, the chromium and manganese can be applied to the catalyst support, for example, by joint precipitation of a manganese-chromium hydroxide mixture from a chromium salt and manganese salt solution with an alkali metal hydroxide solution or ammonia and subsequent washing out of the soluble contents with water. Possible salts of chromium and manganese are, in particular, the sulphates, chlorides acetates and/or nitrates of the elements mentioned. The chromium and manganese can also be precipitated onto the catalyst support as ammonium-manganese chromate or ammonium-alkali metal-manganese chromate from a solution of manganese(II) salts and ammonium bichromate by means of ammonia and/or basic alkali metal compounds. Particularly uniform and firmly adhering precipitates are obtained if the base is added slowly and uniformly, avoiding relatively large differences in concentration. For this, the precipitation can be carried out, for example, by means of urea under hydrolysing conditions, which particularly ensures the conditions of slow addition of the base.

After the application of the chromium compounds and manganese compounds and the precipitation described, the catalyst support charged in this way can be washed free from soluble compounds, before being heated to elevated temperatures (for example 200°–450° C., preferably 250°–350° C.). After this heat treatment, the support charged with chromium and manganese is ready for impregnation with the other catalyst constituents mentioned.

The support is impregnated with the noble metals and with the alkali metal hydroxide and alkali metal sulphate (in each case one or more of these) separately. A procedure can be followed here in which the noble metals are first impregnated onto the support, for example in the form of aqueous solutions of their chlorides, nitrates, acetates or other suitable salts, further impregnation with an alkali metal hydroxide solution and an alkali metal sulphate solution taking place after drying. In this treatment, the noble metals are precipitated in the form of their oxides or hydroxides. The alkali metal hydroxide or hydroxides and the alkali metal sulphates or sulphates can be impregnated on separately or together. After final drying, the catalyst is available. It is preferably activated in the reactor by treatment with hydrogen at elevated temperature, such as at 120°–450° C., preferably at 200°–420° C., before being used.

However, the support can also first be impregnated with an alkali metal hydroxide solution and then dried, and the salts of the noble metals can be applied to the catalyst support which has been pretreated in this way and rendered basic, the precipitation of the noble metals in the form of their oxides or hydroxides also taking place at the time of impregnation. In this variant, the additional impregnation with one or more alkali metal sulphates can be carried out together with the alkali metal hydroxide, before or after application of the alkali metal hydroxide or as a final impregnation after application of the noble metals. In this case also, separate drying is carried out after each impregnation. After the final drying, the catalyst is also ready for use according to this variant, and can be activated beforehand in the manner described using hydrogen at elevated temperature.

Instead of the support mentioned being impregnated with the substances mentioned in order for it to be charged, it can also be sprayed with suitable solutions. The working equipment needed for this as the adjustment of the desired charging by reducing the amount and concentration of the solutions of the elements mentioned are known in principle to the expert.

In addition to aqueous solutions, alcoholic solutions or solutions in lower carboxylic acids or lower amines are in principle also possible, as long as the proposed salts of the noble metals and the basic alkali metal compounds are soluble therein.

The process according to the invention is carried out in the gas phase at a temperature of 250°–500° C., preferably 280°–450° C., particularly preferably 300°–425° C., under a pressure of 10 mbar to 100 bar, preferably 100 mbar to 6 bar, particularly preferably 0.9–1.2 bar. In a manner known to the expert, lower temperatures in the range mentioned are in general assigned to lower pressures in the range also disclosed, and vice versa.

The optionally substituted N-cyclohexylidene-aniline to be reacted can of course be employed as such according to the invention. However, it is of particular advantage that the N-cyclohexylidene-aniline can also be employed as a mixture with other substances. Such other substances are, for example, optionally substituted aniline which is aditionally present and may have originated, for example, from cleavage of the N-cyclohexylidene-aniline, or a mixture of optionally substituted aniline which is additionally present and correspondingly substituted N-cyclohexylaniline.

The N-cyclohexylidene-aniline or its mixture with one or more of the substances mentioned is advantageously brought over the rhodium catalyst with the aid of a carrier gas stream. Examples of such carrier gases are nitrogen, hydrogen, helium, argon, lower hydrocarbons, such as methane, ethane or natural gas, and others, or mixtures of these carrier gases. Nitrogen, methane natural gas or hydrogen or a mixture of these are preferably employed as the carrier gas. The carrier gas is employed in an amount of 1–100 l/g of starting material, preferably 1–50 l/g of starting material. The catalyst loading is specified as 0.01–1 kg of starting material per liter of catalyst per hour, preferably 0.1–0.8, particularly preferably 0.3–0.5.

The process according to the invention is in general carried out continuously in apparatuses such as are known generally to the expert for carrying out reactions of gases over solid contacts industrially.

To charge the gaseous diluent, this is passed through an evaporator for the starting material. Falling film or thin film evaporators of customary design are advantageously used for this.

The working up of the product mixture formed is also known in principle to the expert. The aniline obtained is advantageously re-used for synthesis of the starting material.

The technical progress of the process according to the invention lies in the very high stability of the catalysts under load during dehydrogenation of the N-cyclohexylidene-anilines and their ease and frequency of regeneration, in the complete conversion coupled with a very good selectivity of diphenylamine and the formation of by-products which are easy to remove. Readily accessible starting materials, which can be substituted symmetrically or non-symmetrically, are therefore fed in a simple manner to a conversion which is of industrial interest.

EXAMPLES

EXAMPLE 1

200 g of spherical $\gamma$-$Al_2O_3$ having a diameter of 2-5 mm and a specific surface area of 350 m$^2$/g were initially introduced into a round-bottomed flask, and a solution of 16.6 g of $MnSO_4.4H_2O$, 12.4 g of $(NH_4)_2Cr_2O_7$ and 90 g of urea in 144 ml of water was added. The flask was kept at 85° C. for 1 hour, while being rotated, the liquid which had not been adsorbed was filtered off and the catalyst support was washed free from sulphate and then dried at 110° C. under a water pump vacuum in the course of 25 hours. The catalyst support treated in this way was then heat-treated at 300° C. for 30 minutes.

The catalyst support thus prepared was impregnated with a solution which had been prepared from 5.58 g of $RhCl_3$ and 66 g of water. After intermediate drying, the catalyst was impregnated again with a solution of 5.84 g of NaOH in 60 g of water and dried again.

50 g of the catalyst thus obtained were impregnated with a solution of 1.5 g of $K_2SO_4$ in 15 g of water and finally dried at 100° C. for 18 hours.

30 ml (29 g) of the rhodium-containing catalyst thus prepared were activated in a stream of hydrogen (10 l/hour) at 400° C. for 66 hours in a vertically positioned, electrically heated glass tube of 17 mm internal diameter and 70 cm length. The oven temperature was set at 360° C. and nitrogen (10 l/hour) was used as the carrier gas for dehydrogenation of N-cyclohexylidene-aniline. The N-cyclohexylidene-aniline was passed in from the top in co-current with the carrier gas using a calibrated metering device (~6.5 g/hour). The N-cyclohexylidene-aniline vaporised in the upper part of the reaction tube, which contained only packing, and flowed together with the carrier gas through the catalyst bed, which was in the central section of the reaction tube. The reaction product formed was condensed out and analysed by gas chromatography.

At a catalyst loading of 0.13-0.3 g of N-cyclohexylidene-aniline/ml×hour, the reaction product had the following composition as a function of the operating time of the catalyst (the remainder to make up 100% are by-products):

| Operating time (hours) | 42 | 64 | 407 | 471 |
|---|---|---|---|---|
| Diphenylamine: | 86.1% | 94.0% | 94.4% | 94.3% |
| N-Cyclohexyl-aniline: | — | — | 0.15% | 0.4% |
| Aniline: | 11.8% | 3.3% | 3.5% | 3.4% |

EXAMPLE 2

200 g of a $\gamma$-$Al_2O_3$ in spherical form (2-6 mm) charged with manganese and chromium were impregnated with a solution which had been prepared from 1.58 g of $RhCl_3$, 5.0 g of $PdCl_2$, 1.6 g of concentrated hydrochloric acid and 68 ml of water. The moist catalyst pellets were dried at 120° C. under a water pump vacuum.

The catalyst pellets were first impregnated with a solution of 11 g of KOH and 60 ml of water, and after intermediate drying were impregnated again with a solution of 6 g of $K_2SO_4$ in 60 ml of water and dried again at 120° C.

30 ml (25.3 g) of the catalyst thus prepared were heated to 380° C. in a stream of hydrogen (10 l/hour), using the reaction tube described in Example 1, and were kept at this temperature for 3 hours. The oven temperature was then reduced and the dehydrogenation reaction was carried out at 320° C. 12.4 g of N-cyclohexylidene-aniline and 10 l of nitrogen per hour were passed together over the catalyst. The reaction product had the following composition (the remainder to make up 100% are by-products):

| | |
|---|---|
| Diphenylamine: | 85.2% |
| Cyclohexylidene-aniline: | 1.2% |
| N-Cyclohexyl-aniline: | 3.4% |
| Aniline: | 6.7% |

EXAMPLE 3

200 g of a $\gamma$-$Al_2O_3$ in the form of pellets charged with chromium and manganese were impregnated uniformly with a solution of 2.64 g of $RhCl_3$ and 3.33 g of $H_2PtCl_6$ in 60 ml of water in a round-bottomed flask. The moist catalyst pellets were dried at 120° C. under a water-pump vacuum, reduction was then carried out in a stream of hydrogen (30 l of $H_2$/hour) at 400° C. for 8 hours and the pellets were then washed free from chloride at room temperature. The catalyst was dried again and impregnated with a solution which had been prepared from 6 g of NaOH, 6 g of $K_2SO_4$ and 76 g of water. After this impregnation, the catalyst was dried again.

A reaction tube having a diameter of 17 mm and a length of about 600 mm, the upper part of which served as a vaporisation zone and which was filled in the lower part with 30 ml (26.7 g) of the catalyst prepared, was kept at 400° C. by electrical heating. The catalyst was first activated in a stream of $H_2$ (10 l/hour) at this temperature for 72 hours. 76 g of N-cyclohexylidene-aniline and 10 l of $H_2O$/hour were then passed into the reaction tube in the course of 15 hours, using a calibrated metering device. The reaction product was condensed and analysed by gas chromatography. The following composition resulted as the average of the reaction run of 15 hours (the remainder to make up 100% are by-products):

| | |
|---|---|
| Diphenylamine: | 92.1% |
| N-Cyclohexyl-aniline: | 0.3% |
| Aniline: | 4.2% |

EXAMPLE 4

2.3 l of the catalyst described in EP 208,933, Example 5, were introduced into a tube of 2.5 m length and 4 cm diameter which was thermostatically controlled by resistance heating. The length of the catalyst bed was 156 cm. The catalyst was dried in a dry stream of nitrogen at 200° C. for 12 hours and treated in a stream of hydrogen at 300° C. for 24 hours.

The reaction tube was connected to a circulating falling film evaporator 2 m long, through which a dry stream of nitrogen of 600 l of nitrogen per hour was passed. 2000 ml of N-cyclohexylidene-aniline were pumped in circulation through the falling film evaporator, the temperature inside the evaporator being slowly increased until 700 g of educt per hour vaporised. The educt fed in consisted to the extent of 99% of N-cyclohexylidene-aniline and to the extent of 1% of aniline. The temperature gradient in the tube reactor was adjusted so that the minimum temperature did not fall below 350° C. and the maximum temperature did not exceed 410° C. When the reaction product was condensed and analysed by gas chromatography, it showed the following dependence of the composition on time:

| Operating hours | 100 | 200 | 1000 | 2000 |
|---|---|---|---|---|
| Diphenylamine | 95.9 | 96.5 | 97.0 | 95.5 |
| N-Cyclohexyl-aniline | 0.15 | 0.07 | 0.05 | 0.15 |
| N-Cyclohexylidene-aniline | 0.15 | — | — | 0.24 |
| Aniline | 2.1 | 2.0 | 1.55 | 1.9 |
| Benzene | 1.1 | 0.9 | 0.8 | 1.5 |
| High-boiling constituents*) | 0.6 | 0.6 | 0.6 | 0.7 |

*)Carbazole, 2-phenyl-diphenylamine, phenylcarbazole

After 2000 hours, the catalyst was freed from carbon-rich deposits by burning, and after reductive treatment with hydrogen at 350° C. had the activity of a fresh catalyst.

EXAMPLE 5

N-Cyclohexylidene-3-methyl-aniline was reacted in the apparatus described in Example 4 under the same conditions. When the reaction product was condensed and analysed by gas chromatography, it showed the following dependences of the composition on time:

| Operating hours | 100 | 200 | 1000 | 2000 |
|---|---|---|---|---|
| 3-Methyl-diphenylamine | 95.4 | 95.5 | 95.9 | 95.1 |
| N-Cyclohexyl-3-methyl-aniline | 0.25 | 0.1 | 0.08 | 0.18 |
| N-Cyclohexylidene-3-methyl-aniline | 0.05 | — | — | 0.08 |
| 3-Methyl-aniline | 2.3 | 2.1 | 1.9 | 2.1 |
| Benzene | 1.2 | 1.4 | 1.3 | 1.5 |
| High-boiling constituents*) | 0.8 | 0.9 | 0.8 | 1.0 |

*)Methylcarbazole, methyl-phenyl'-diphenylamine, methyl-phenyl'-carbazole

EXAMPLE 6

2.4 l of the catalyst described in German Offenlegungsschrift 3,801,754, Example 2, were introduced into the apparatus described in Example 4 and were activated. At a minimum temperature of 380° C. and a maximum temperature of 420° C. in the catalyst bed, the other conditions described in Example 1 were observed. When the reaction product was condensed and analysed by gas chromatography, it showed the following dependence of the composition on time:

| Operating hours | 100 | 200 | 1000 | 2000 |
|---|---|---|---|---|
| Diphenylamine | 96.7 | 97.2 | 97.4 | 96.9 |
| N-Cyclohexyl-aniline | 0.06 | 0.01 | 0.02 | 0.1 |
| N-Cyclohexylidene-aniline | — | — | — | 0.02 |
| Aniline | 1.5 | 1.2 | 1.0 | 1.2 |
| Benzene | 0.9 | 0.8 | 0.6 | 0.9 |
| High-boiling constituents*) | 0.8 | 0.8 | 1.0 | 0.9 |

*)Carbazole, phenyl-diphenylamine, phenylcarbazole.

What is claimed is:

1. A process for the preparation of a diphenylamine of the formula

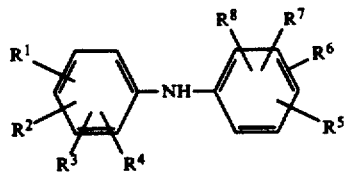

in which
R$^1$ represents hydrogen, C$_1$-C$_6$-alkyl, C$_1$-C$_2$-alkoxy, C$_3$-C$_6$-cycloalkyl, benzyl or aryl,
R$^2$ represents hydrogen, C$_1$-C$_6$-alkyl or C$_1$-C$_2$-alkoxy,
R$^5$ denotes hydrogen, C$_1$-C$_6$-alkyl, C$_1$-C$_6$-alkoxy, C$_3$-C$_6$-cycloalkyl, benzyl, aryl, hydroxyl, amino, C$_1$-C$_6$-alkylamino, di-C$_1$-C$_6$-alkylamino, aryloxy or arylamino,
R$^6$ represents hydrogen, C$_1$-C$_6$-alkyl, C$_1$-C$_6$-alkoxy, hydroxy, amino or C$_1$-C$_6$-alkylamino and
R$^3$, R$^4$, R$^7$ and R$^8$ independently of one another denote hydrogen or C$_1$-C$_2$-alkyl,
wherein aryl represents phenyl or represents 5- or 6-membered heteroaryl which has 1 or 2 hetero atoms from the group comprising N, O and S and is bonded in the 2-, 3- or 4-position, wherein a N-cyclohexylidene-aniline of the formula

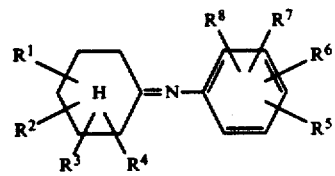

in which the radicals R$^1$ and R$^8$ have the above meaning, and which can be in admixture with a gaseous diluent, is dehydrogenated at 250°-500° C. on a catalyst which has a rhodium content of 0.05-5% by weight, it being possible for up to 90% by weight of the rhodium content to be replaced by one or more platinum metals from the group comprising palladium, platinum and iridium, and which furthermore contains additions of 1-6% by weight of an alkali metal hydroxide and 1-6% by weight of an alkali metal sulphate, and all the percentages being based on the total weight of the catalyst.

2. The process of claim 1, wherein the catalyst has a rhodium content of 0.05-4% by weight.

3. The process of claim 2, wherein the catalyst has a rhodium content of 0.1-3% by weight.

4. The process of claim 1, wherein the catalyst support is Al$_2$O$_3$ or an aluminium spinel.

5. The process of claim 1, wherein the catalyst support is an aluminium oxide or aluminium spinel treated with chromium and manganese.

6. The process of claim 1, wherein the catalyst support has a surface area of greater than 100 m$^2$/g.

7. The process of claim 1, which is carried out in a temperature range of 280°–450° C.

8. The process of claim 7, which is carried out in a temperature range of 300°–425° C.

9. The process of claim 1, which is carried out in a pressure range between 10 mbar and 100 bar.

10. The process of claim 9, which is carried out in a pressure range of 100 mbar to 2 bar.

11. The process of claim 10, which is carried out in a pressure range of 0.9 to 1.2 bar.

12. The process of claim 1, wherein a gas selected from the group consisting of hydrogen, methane, ethane, nitrogen, natural gas, helium and argon is used as the gaseous diluent.

13. The process of claim 1, wherein the amount of the gaseous diluent or carrier gas is 0.1–20 mol per mol of starting compound.

14. The process of claim 13, wherein the amount of the gaseous diluent is 1–10 mol per mol of starting compound.

15. The process of claim 14, wherein the amount of the gaseous diluent is 4–8 mol per mol of starting compound.

16. The process of claim 1, wherein the catalyst loading is 0.01–1 g/ml/hour.

17. The process of claim 17, wherein the catalyst loading is 0.1–0.8 g/ml/hour.

18. The process of claim 17, wherein the catalyst loading is 0.3–0.5 g/ml/hour.

19. The process of claim 1, wherein a N-cyclohexylidene-aniline of the formula

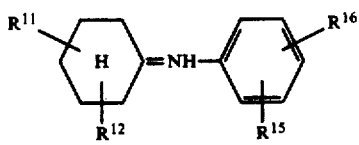

is employed in which
 $R^{11}$ denotes hydrogen, $C_1$–$C_6$-alkyl, $C_1$–$C_2$-alkoxy, cyclopropyl, cyclopentyl, cyclohexyl or phenyl,
 $R^{12}$ denotes hydrogen, $C_1$–$C_2$-alkyl or $C_1$–$C_2$-alkoxy,
 $R^{15}$ denotes hydrogen, $C_1$–$C_6$-alkyl, $C_1$–$C_4$-alkoxy, cyclopropyl, cyclopentyl, cyclohexyl, phenyl, hydroxyl, amino, $C_1$–$C_6$-alkylamino, di-$C_1$–$C_4$-alkylamino, phenoxy or phenylamino and
 $R^{16}$ denotes hydrogen, $C_1$–$C_2$-alkyl or $C_1$–$C_2$-alkoxy.

20. The process of claim 19, wherein a N-cyclohexylidene-aniline of the formula

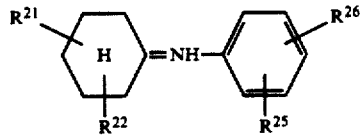

is employed in which
 $R^{21}$, $R^{22}$ and $R^{26}$ independently of one another denote hydrogen, methyl or ethyl and
 $R^{25}$ represents hydrogen, methyl, ethyl, methoxy, ethoxy, $C_1$–$C_6$-alkylamino or di-$C_1$–$C_6$-alkylamino.

* * * * *

UNITED STATES PATENT AND TRADEMARK OFFICE
CERTIFICATE OF CORRECTION

PATENT NO. : 5,196,592
DATED : March 23, 1993
INVENTOR(S) : Immel, et al.

It is certified that error appears in the above-identified patent and that said Letters Patent is hereby corrected as shown below:

Col. 11, line 31    After " of " delete " claim 17 " and substitute -- claim 16 --

Col. 12, last line  Delete " di-$C_1$-$C_6$-alkylamino " and substitute -- di-$C_1$-$C_2$-alkylamino --

Signed and Sealed this

Sixteenth Day of August, 1994

Attest:

BRUCE LEHMAN

*Attesting Officer*     Commissioner of Patents and Trademarks